United States Patent [19]

Canty

[11] 4,323,062
[45] Apr. 6, 1982

[54] SURGICAL DRAPE WITH RETAINING DEVICE

[75] Inventor: Herbert G. Canty, Ingleside, Ill.

[73] Assignee: The Kendall Company, Boston, Mass.

[21] Appl. No.: 210,887

[22] Filed: Nov. 28, 1980

[51] Int. Cl.³ ............................................. A61F 13/00
[52] U.S. Cl. .................................. 128/132 D; 128/292
[58] Field of Search ................. 128/132 R, 132 D, 292

[56] References Cited

U.S. PATENT DOCUMENTS

| | | | |
|---|---|---|---|
| 3,364,928 | 1/1968 | Creager et al. | 128/132 D |
| 3,422,817 | 1/1969 | Mishkin et al. | 128/132 D |
| 3,452,750 | 7/1969 | Blanford | 128/132 D |
| 3,503,391 | 3/1970 | Melges | 128/132 D |
| 3,738,359 | 6/1973 | Lindquist et al. | 128/132 D |
| 3,791,382 | 2/1974 | Collins | 128/132 D |
| 3,800,790 | 4/1974 | Collins | 128/132 D |
| 3,881,474 | 5/1975 | Krzewinski | 128/132 D |
| 3,926,185 | 12/1975 | Krzewinski | 128/132 D |
| 4,076,017 | 2/1978 | Haswell | 128/132 D |
| 4,089,331 | 5/1978 | Hastigan et al. | 128/132 D |

Primary Examiner—Robert W. Michell
Assistant Examiner—C. W. Shedd
Attorney, Agent, or Firm—Powell L. Sprunger

[57] ABSTRACT

A drape for performing a surgical procedure on a patient's body comprising, a main sheet for placement over the patient's body, with the main sheet having an inner surface facing toward the patient's body after placement of the drape, and an outer surface facing away from the patient's body after placement of the drape. The drape has a pocket on the outer surface of the main sheet, with the pocket being spaced from the site of surgical procedure and being positioned in the expected path of fluid runoff during the surgical procedure. The pocket has a flap defining a pouch and an outer edge defining an opening communicating with the pouch. The flap has a device for retaining tubing or the like during the surgical procedure.

22 Claims, 9 Drawing Figures

U.S. Patent  Apr. 6, 1982  4,323,062
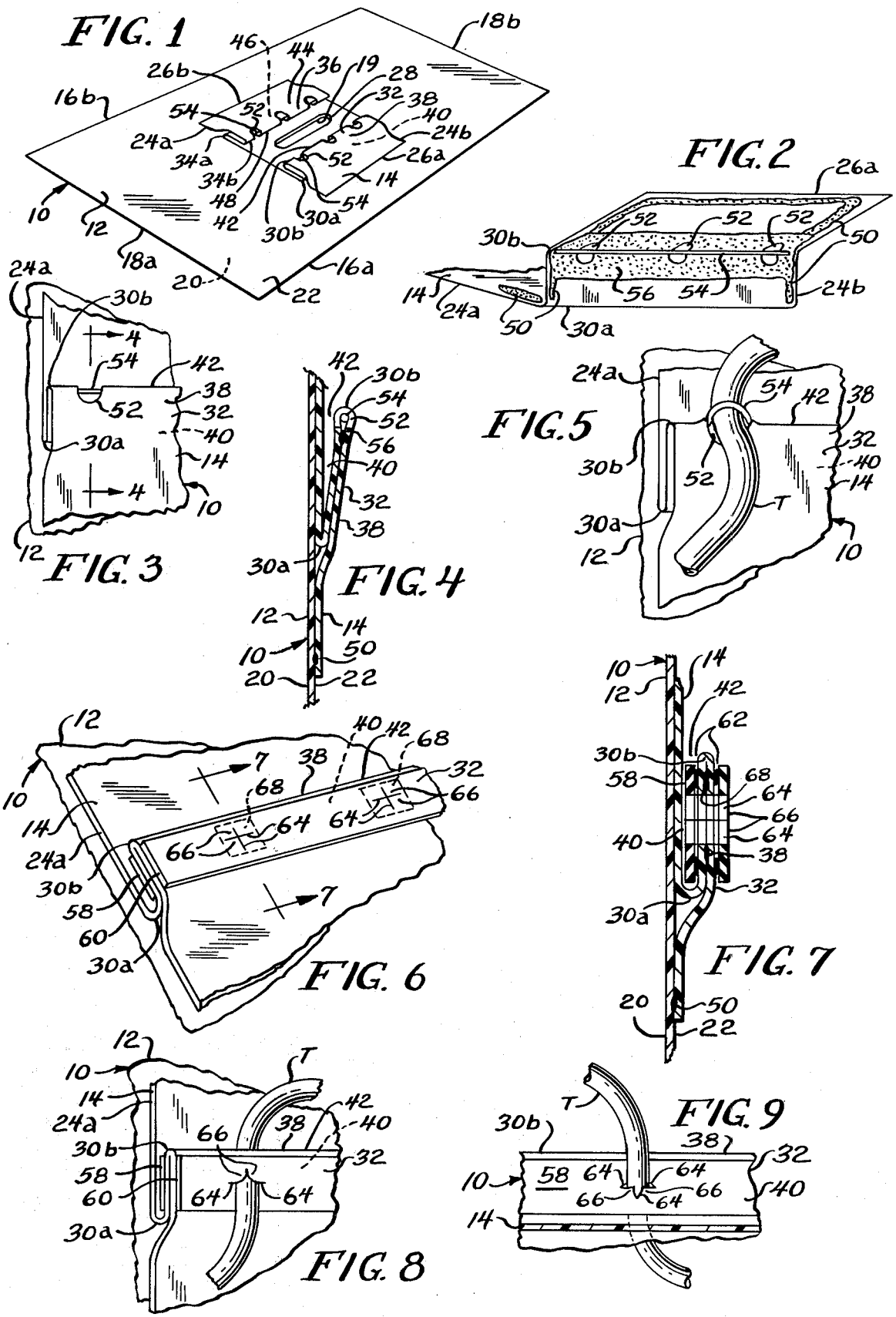

SURGICAL DRAPE WITH RETAINING DEVICE

BACKGROUND OF THE INVENTION

The present invention relates to disposable articles, and more particularly to surgical drapes.

An assortment of disposable drapes have been proposed for use during surgical procedures and operations. Such drapes normally have a sheet with a fenestration for placement over the surgical site. During certain operations, e.g., open heart surgery, tubes and other equipment of a similar nature may pass over the drape to the surgical site. Examples of such equipment include tubing for a heart-lung machine, aspiration tubing, fibrillator cord, defibrillator cord, pacing cord, etc. Of course, it is necessary to secure such tubes or cords in place on the drape to prevent them from moving relative the surgical site and from obstructing the surgeon during the operation.

If clips are attached directly to the drape, they may puncture the drape and destroy the sterile barrier required over the patient, a procedure sometimes practiced. Hence, certain surgeons place loose linens over the drape and use clips to attach the equipment to the linens. However, this procedure is inconvenient and time-consuming, and the linens do not totally prevent movement of the equipment.

SUMMARY OF THE INVENTION

A principal feature of the present invention is the provision of a surgical drape which permits securement of auxiliary equipment to the drape in a sure and simplified manner.

The drape of the present invention comprises, a main sheet for placement over the patient's body, with the main sheet having an inner surface facing toward the patient's body after placement of the drape, and an outer surface facing away from the patient's body after placement of the drape. The drape has a pocket on the outer surface of the main sheet, with the pocket being spaced from the site of surgical procedure and being positioned in the expected path of fluid runoff during the surgical procedure. The pocket has a flap defining a pouch and an outer edge defining an opening communicating with the pouch.

A feature of the present invention is that the flap has a device for securing tubing or the like to the drape during the surgical procedure.

Another feature of the invention is that in one embodiment the retaining device comprises an aperture extending through the flap, and an elastic strip extending across the aperture.

Yet another feature of the invention is that the strip engages against the tubing or the like placed in the flap aperture.

Still another feature of the invention is that in another embodiment the retaining device comprises slit means extending through the flap.

Another feature of the invention is that the slit means in the flap receives tubing or the like through the flap and retains it in place.

A further feature of the invention is the provision of a sheet of relatively high friction material on at least one side of the flap to frictionally engage the tubing or the like passing through the slit means.

Further features will become more fully apparent in the following description of the embodiments of this invention and from the appended claims.

DESCRIPTION OF THE DRAWINGS

In the drawings:

FIG. 1 is a perspective view of an embodiment of a surgical drape of the present invention;

FIG. 2 is a fragmentary perspective view illustrating formation of a flap on the drape of FIG. 1;

FIG. 3 is a fragmentary plan view on an enlarged scale of the drape of FIG. 1;

FIG. 4 is a fragmentary sectional view taken substantially as indicated along the line 4—4 of FIG. 3;

FIG. 5 is a fragmentary plan view showing use of the drape flap to secure tubing or the like in place;

FIG. 6 is a fragmentary perspective view of another embodiment of the drape of the present invention;

FIG. 7 is a fragmentary sectional view taken substantially as indicated along the line 7—7 of FIG. 6;

FIG. 8 is an outer plan view showing use of slit means in a flap of the drape of FIG. 6 to secure tubing or the like in place; and FIG. 9 is an inner perspective view showing the tubing or the like secured in the drape flap.

DESCRIPTION OF THE PREFERRED EMBODIMENTS

Referring now to FIGS. 1–4, there is shown a surgical drape generally designated 10 having a main sheet 12 and a reinforcement sheet 14. The main sheet 12 has a pair of side edges 16a and 16b, a pair of end edges 18a and 18b connecting the side edges 16a and b, a fenestration 19, an inner surface 20 facing toward the patient after placement of the drape 10, and an outer surface 22 facing away from the patient after placement of the drape 10. The main sheet 12 and reinforcement sheet 14 may comprise any suitable flexible material, such as a nonwoven material.

The reinforcement sheet 14 has a pair of side edges 24a and 24b, and a pair of end edges 26a and 26b connecting the side edges 24a and b, with the reinforcement sheet 14 having a fenestration 28 in alignment with the fenestration 19 of the main sheet 12. As shown, the reinforcement sheet 14 has a pair of aligned fold lines 30a and 30b defining a pocket 32 on the outer surface of the main sheet 12 on one side of the fenestrations 19 and 28, and a pair of aligned fold lines 34a and 34b defining a pocket 36 on the outer surface of the main sheet 12 on the other side of the fenestrations 19 and 28. The pocket 32 has a flap 38 comprising the doubled reinforcement sheet 14, with the flap 38 defining a pouch 40 beneath the flap 38, with the fold line 30b of the flap 38 defining an outer edge of the flap 38, and with the outer edge 30b defining an opening 42 facing toward the fenestrations 19 and 28 and communicating with the pouch 40. Similarly, the pocket 36 has a flap 44 comprising the doubled reinforcement sheet 14, with the flap 44 defining a pouch 46 beneath the flap 44, with the fold line 34b of the flap 44 defining an outer edge of the flap 44, and with the outer edge 34b defining an opening 48 facing toward the fenestrations 19 and 28 and communicating with the pouch 46. The reinforcement sheet 14 may be secured in place on the outer surface 22 of the main sheet 12 in the folded configuration to form the pockets 32 and 36 by suitable adhesive lines 50 as described in U.S. Pat. No. 3,791,382, incorporated herein by reference.

The retaining means of the present invention will be described in connection with the pocket 32, although the pocket 36 also has similar retaining means, as will be evident from the drawings. As shown, the flap 38 of pocket 32 has a plurality of spaced cutouts 52 located at the fold line or outer edge 30b of the flap 38, with the cutouts 52 extending through both sheets of doubled material in the flap 38 and forming apertures of generally semi-circular shape which are spaced along the fold line 30b. The flap 38 has an elastic strip or band 54 extending along the fold line 30b intermediate the doubled sheet of the flap 38, such that the strip 54 extends across the apertures or cutouts 42 in the folded flap 38. As shown, the reinforcement sheet 14 has adhesive 56 extending around the apertures or cutouts 52 and along the fold line 30b in order to secure the elastic strip 54 in place and reinforce the apertures or cutouts 52 around the apertures or cutouts 52. In a preferred form, the elastic strip 54 is placed under tension in order to cause a slight flaring of the flap 38 along the outer edge or fold line 30b to facilitate passage of liquid into the pouch 40 of the pocket 32.

In use, the drape 10 is placed over the patient's body, with the fenestrations 19 and 28 located over the surgical site. During the surgical procedure, body fluids, such as blood, flow through the fenestrations 19 and 28 and into the pockets 32 and 36 for retention therein. With reference to FIG. 5, tubing T or the like may be passed through the apertures or cutouts 52 such that the elastic strip 54 extending across the cutouts 52 frictionally engages against the tubing T and retains it in place during the surgical procedure. In this manner, the drape 10 of the present invention provides means in the pockets 32 and 36 which readily receive tubing T or the like and retains it in place during the surgical procedure. As will be apparent, the retaining means in the pockets 32 and 36 may be formed in a simplified manner, and may be constructed at a reduced cost.

Another embodiment of the present invention is illustrated in FIGS. 6–9, in which like reference numerals designate like parts. In this embodiment, the reinforcement sheet 14 is folded and secured in place in a manner as previously described in connection with the drape of FIGS. 1–5 to form a pair of pockets which receive fluid runoff during a surgical procedure from the fenestrations. As shown in FIGS. 6 and 7, the flap 38 has a pair of elongated sheets 58 and 60 of relatively high friction material, such as latex, on opposed sides of the flap 38. The sheets 58 and 60 may be secured to the flap 38 by suitable means, such as adhesive 62. As shown, the flap 38 has a plurality of sets of spaced cross slits 64 which define a plurality of spaced sets of four gripping tabs 66 intermediate the associated cross slits 64, with the cross slits 64 extending through the flap 38 and high friction sheets 58 and 60, and with the cross slits being spaced from the outer edge 30b. The flap 38 has regions of adhesive 68 intermediate the doubled sheet of the flap 38 and surrounding the cross slits 64 in order to reinforce the tabs 66.

In use, the drape 10 is placed over the patient's body with the fenstrations located at the site of the surgical procedure, such that the pockets on the drape 10 receive fluid runoff from the fenestrations in a manner as previously described in connection with the drape of FIGS. 1–5. As shown in FIGS. 8 and 9, the cross slits 64 receive tubing T or the like, such that the tabs 66 frictionally engage against the wall of the tubing T or the like to retain it in place, with the sheets 58 and 60 of relatively high friction material enhancing the frictional engagement between the tabs 66 and the tubing T or the like. Thus, in accordance with the present invention, the tubing T or the like may be readily threaded through the cross slits 64 in the flap 38 in order to receive and retain the tubing T or the like in place during the surgical procedure. Of course, the other pocket 36 may also have suitable cross slits defining tabs in the manner described in connection with the pocket 32.

The foregoing detailed description is given for clearness of understanding only, and no unnecessary limitations should be understood therefrom, as modifications will be obvious to those skilled in the art.

I claim:

1. A drape for performing a surgical procedure on a patient's body, comprising:
   a main sheet for placement over the patient's body, said main sheet having an inner surface facing toward the patient's body after placement of the drape, and an outer surface facing away from the patient's body after placement of the drape; and
   a pocket on the outer surface of said main sheet, said pocket being spaced from the site of surgical procedure and being positioned in the expected path of fluid runoff during the surgical procedure, said pocket having a flap defining a pouch and an outer edge defining an opening communicating with said pouch, said flap having an aperture extending through the flap, and an elastic strip extending across the aperture to engage against tubing or the like placed in the flap aperture.

2. The drape of claim 1 wherein said aperture is located at said outer edge of the flap.

3. The drape of claim 2 wherein said aperture has a generally semicircular shape.

4. The drape of claim 2 wherein said strip comprises a relatively narrow band extending along said outer edge.

5. The drape of claim 4 wherein said strip extends substantially the length of said flap.

6. The drape of claim 5 wherein said strip is placed under tension.

7. The drape of claim 5 including a plurality of spaced apertures at the outer edge of the flap, said strip extending across said plural apertures.

8. The drape of claim 1 including a plurality of spaced apertures in said flap, with said strip extending across said apertures.

9. The drape of claim 1 wherein said flap comprises a doubled sheet with a fold line in said doubled sheet defining said outer edge.

10. The drape of claim 9 including adhesive between said doubled sheet and surrounding said aperture.

11. The drape of claim 9 wherein said strip comprises a relatively narrow band extending along said fold line between said doubled sheet.

12. The drape of claim 1 wherein said flap comprises a reinforcement sheet for the main sheet.

13. A drape for performing a surgical procedure on a patient's body, comprising:
   a main sheet for placement over the patient's body, said main sheet having a pair of side edges, a pair of end edges connecting the side edges, a fenestration, an inner surface facing toward the patient's body after placement of the drape, and an outer surface facing away from the patient's body after placement of the drape; and a pocket on the outer surface of said main sheet, said pocket being spaced from the fenestration and being positioned intermediate said fenestration and one of said side edges in the expected path of fluid runoff from the surgical site during the surgical procedure, said pocket having a flap comprising a doubled sheet defining a pouch, with said flap having a fold line defining an outer edge of the pocket and an opening communicating with the pouch, said flap having a plurality of cutouts in the doubled sheet adjacent the fold line defining spaced apertures at the outer edge of the flap, and said flap having an elastic band extending along the fold line between the doubled sheet and extending across said apertures to grip tubing or the like placed in said apertures.

14. A drape for performing a surgical procedure on a patient's body, comprising:
a main sheet for placement over the patient's body, said main sheet having an inner surface facing toward the patient's body after placement of the drape, and an outer surface facing away from the patient's body after placement of the drape; and
a pocket on the outer surface of said main sheet, said pocket being spaced from the site of surgical procedure and being positioned in the expected path of fluid runoff during the surgical procedure, said pocket having a flap defining a pouch and an outer edge defining an opening communicating with said pouch, said flap having slit means spaced from the outer edge and being sufficiently large to receive tubing or the like through said flap.

15. The drape of claim 14 wherein said slit means comprises a pair of cross slits defining a plurality of tabs.

16. The drape of claim 14 including a sheet of relatively high friction material surrounding the slit means on at least one side of the flap.

17. The drape of claim 16 including a sheet of relatively high friction material surrounding the slit means on both sides of the flap.

18. The drape of claim 16 wherein said high friction material comprises latex.

19. The drape of claim 14 wherein said flap comprises a doubled sheet having a fold line defining said outer edge.

20. The drape of claim 19 including adhesive intermediate the doubled sheet and surrounding the slit means.

21. The drape of claim 14 wherein said flap comprises a reinforcement sheet for the main sheet.

22. A drape for performing a surgical procedure on a patient's body, comprising:
a main sheet for placement over the patient's body, said main sheet having a pair of side edges, a pair of end edges connecting the side edges, a fenestration, an inner surface facing toward the patient's body after placement of the drape, and an outer surface facing away from the patient's body after placement of the drape; and
a pocket on the outer surface of said main sheet, said pocket being spaced from the fenestration and being position intermediate said fenestration and one of said side edges in the expected path of fluid runoff from the surgical site during the surgical procedure, said pocket having a flap comprising a doubled sheet defining a pouch, with said flap having a fold line defining an outer edge of the pocket and an opening communicating with said pouch, said flap having a plurality of spaced cross slits defining tabs to receive tubing or the like through the cross slits.

* * * * *